United States Patent
Thirasak et al.

(10) Patent No.: US 10,435,340 B2
(45) Date of Patent: Oct. 8, 2019

(54) PROCESS FOR THE ENHANCED SEPARATION OF ETHYLBENZENE

(71) Applicants: SCG CHEMICALS COMPANY LIMITED, Bangkok Metropolis (TH); GTC Technology US, LLC, Houston, TX (US)

(72) Inventors: Attapong Thirasak, Bangkok Methropolis (TH); Alisa Kammafoo, Bangkok Methropolis (TH); Wiroon Tanthapanichakoon, Bangkok Methropolis (TH); Zhongyi Ding, Katy, TX (US); Sachin Joshi, Katy, TX (US); Cole Nelson, Cypress, TX (US); Arnat Prombunglum, Bangkok Methropolis (TH)

(73) Assignees: SCG CHEMICALS CO., LTD., Bangkok (TH); GTC TECHNOLOGY US, LLC, Houston, TX (US)

( * ) Notice: Subject to any disclaimer, the term of this patent is extended or adjusted under 35 U.S.C. 154(b) by 16 days.

(21) Appl. No.: 15/505,590

(22) PCT Filed: Sep. 5, 2014

(86) PCT No.: PCT/US2014/054404
§ 371 (c)(1),
(2) Date: Feb. 21, 2017

(87) PCT Pub. No.: WO2016/036392
PCT Pub. Date: Mar. 10, 2016

(65) Prior Publication Data
US 2017/0247303 A1    Aug. 31, 2017

(51) Int. Cl.
*C07C 7/08* (2006.01)
*B01D 53/00* (2006.01)
(Continued)

(52) U.S. Cl.
CPC .............. *C07C 7/08* (2013.01); *B01D 53/002* (2013.01); *C07C 15/073* (2013.01); *C08K 3/16* (2013.01); *C08K 3/30* (2013.01); *C08K 5/16* (2013.01)

(58) Field of Classification Search
CPC ....................................................... C07C 7/08
(Continued)

(56) References Cited

U.S. PATENT DOCUMENTS 2,532,031 A    11/1950  Nixon et al.
3,105,017 A     9/1963  Amir et al.
(Continued)

FOREIGN PATENT DOCUMENTS

CN    1077560 C    1/2002
GB    1198592 A    7/1970
(Continued)

OTHER PUBLICATIONS

First Office Action for Japanese Patent Application No. 2017-533157, dated Apr. 24, 2018, with English translation (7 pages).
(Continued)

*Primary Examiner* — Thuan D Dang
(74) *Attorney, Agent, or Firm* — Dorsey & Whitney LLP

(57) ABSTRACT

A process for the distillative separation of ethylbenzene from a mixture comprising ethylbenzene and at least one other C8 aromatic compound, comprising introducing a feed stream comprising said mixture into a first distillation column, introducing a first stream comprising a heavy solvent above the feed stream into the first distillation column, introducing an aqueous stream below the feed stream into the first distillation column.

19 Claims, 1 Drawing Sheet

(51) Int. Cl.
*C07C 15/073* (2006.01)
*C08K 3/16* (2006.01)
*C08K 3/30* (2006.01)
*C08K 5/16* (2006.01)

(58) Field of Classification Search
USPC ........ 585/833, 856, 857, 860, 862, 863, 868
See application file for complete search history.

(56) References Cited

U.S. PATENT DOCUMENTS

| | | |
|---|---|---|
| 3,684,665 A | 8/1972 | Abe et al. |
| 4,299,668 A | 11/1981 | Berg |
| 5,135,620 A | 8/1992 | Brown |
| 5,425,855 A | 6/1995 | Berg |
| 5,849,982 A | 12/1998 | Lee et al. |
| 2010/0305382 A1 | 12/2010 | Stabel et al. |

FOREIGN PATENT DOCUMENTS

| | | |
|---|---|---|
| JP | H11509868 A | 8/1999 |
| RU | 2670963 C2 | 10/2018 |
| SU | 1097191 A3 | 6/1984 |
| WO | 9744298 | 11/1997 |
| WO | 2016036392 A1 | 3/2016 |

OTHER PUBLICATIONS

First Office Action for Russian Application No. 2017111207, dated May 17, 2018, with English translation (11 pages).
International Search Report and Written Opinion of the International Searching Authority of International Patent Application No. PCT/US2014/054404, dated May 8, 2015 (9 pages).
First Examination Report for Indian Patent Application No. 201717007569, dated Jan. 1, 2019, with English translation (6 pages).
First Office Action for Chinese Patent Application No. 2014800816111, dated Jun. 20, 2019, with English Translation (14 pages).
He, Zicheng (2007). Principles of Chemical Engineering. China Medical Science Press. pp. 294-295 (with English translation).

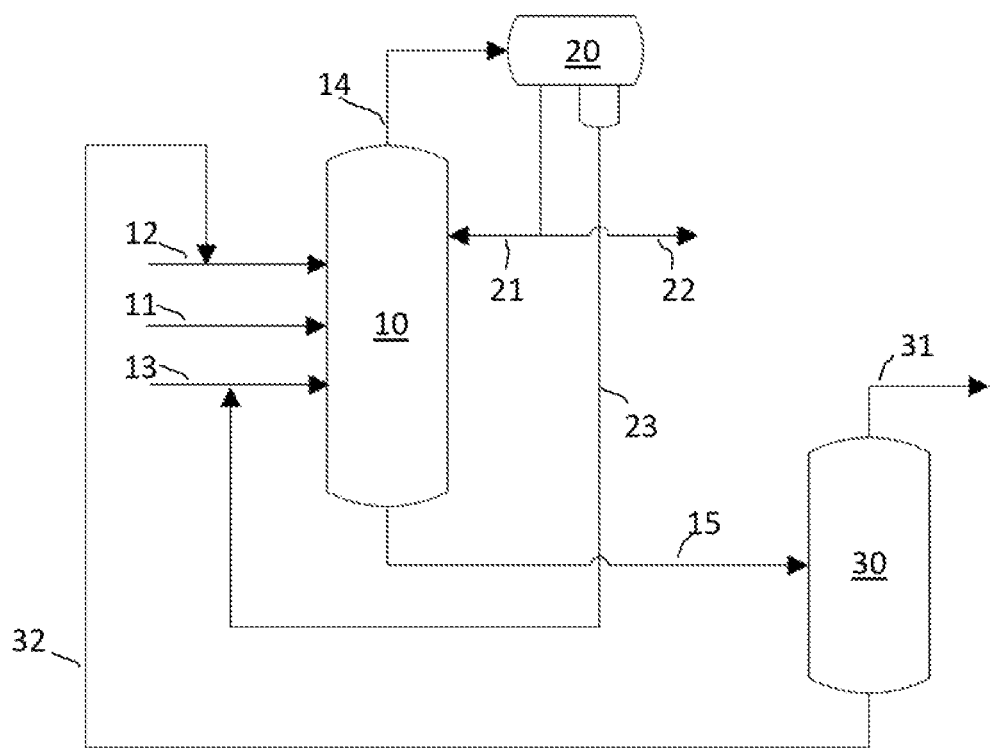

PROCESS FOR THE ENHANCED SEPARATION OF ETHYLBENZENE

The present invention relates to a process for the distillative separation of ethylbenzene from a mixture comprising ethylbenzene and at least one other $C_8$ aromatic compound.

Ethylbenzene is a hydrocarbon compound with high commercial utilization and value. It is majorly used to produce styrene which is an intermediate for polystyrene production. Ethylbenzene may be obtained from alkylation reaction between benzene and ethylene. An alternative way for producing ethylbenzene is to recover it from a hydrocarbon mixture containing ethylbenzene which is generally produced as a byproduct stream from several petrochemical processes. The hydrocarbon mixture containing ethylbenzene usually also contain one or more hydrocarbon compounds with boiling point close to boiling point of ethylbenzene, especially GB aromatic isomers.

Separation of close boiling compounds usually requires a process more sophisticated than conventional distillation. Extractive distillation is one of the techniques developed for this purpose. It has been applied industrial processes, and is becoming a more and more important separation method in petrochemical industries. The main characteristic of extractive distillation is that usually a solvent with high boiling-point is added to the mixture of the components to be separated as an extractive agent, so as to increase the relative volatility of the targeted components.

Relative volatility is a measure of the differences between the vapor pressure of the more volatile component and the vapor pressure of the less volatile component in a liquid mixture. It indicates the degree of separability of two components in the mixture. Besides altering the relative volatility, the extractive agent should also be easily separable from the distillation products, that is, a high boiling point difference between the extractive agent and the components to be separated is desirable. The extractive agent plays an important role in the design of extractive distillation. Therefore, the selection of a suitable extractive agent is essential to ensure an effective and economical design.

Attempts have been made to separate ethylbenzene from a hydrocarbon mixture. GB 1,198,592 describes a process for separating C8 aromatic isomers using a single polyfunctional distillation column. The distillation is carried out in a multiplate column having at least 250 and preferably 365 trays, and a reflux ratio from 100:1 to 250:1 in order to achieve high purity ethylbenzene product. A large distillation column is known to have high cost of construction and consumes high amount of energy during operation.

U.S. Pat. No. 3,105,017 describes a method for separating a C8 aromatic hydrocarbon mixture by distilling said mixture in the presence of a compound containing a single benzene ring substituted on the ring in at least two positions with a chloro group under conditions to separate a fraction enriched with ethylbenzene. However, this method does not provide a high separation efficiency.

U.S. Pat. No. 4,299,668 describes a method for separating ethylbenzene from para-xylene and/or meta-xylene in a rectification column in the presence of an extractive agent comprising pentachlorophenol as a main component with one or more other compounds. Pentachlorophenol appears as white crystalline solid at room temperature with a high melting point, therefore the method of U.S. Pat. No. 4,299,668 requires an additional step and energy for dissolving of pentachlorophenol in a suitable solvent before using it as an extractive agent. Moreover, pentachlorophenol is extremely toxic to humans from acute ingestion and inhalation exposure.

U.S. Pat. No. 5,425,855 discloses the use of 5-methyl-2-hexanone as extractive agent in distillation. It has been found that this agent improves the relative volatility of ethylbenzene to p-xylene, and permits separation of ethylbenzene from p-xylene by rectification.

However, there is still the need for an improved process for the distillative separation of ethylbenzene from a mixture comprising ethylbenzene and at least one other $C_8$ aromatic compound, such as o-xylene, p-xylene, m-xylene or mixtures thereof.

It is thus an object of the invention to provide a process for the enhanced distillative separation of ethylbenzene from a mixture comprising ethylbenzene and at least one other $C_8$ aromatic compound which allows obtaining ethylbenzene in high purity and achieves a high separation efficiency.

It is a further object of the invention to increase the relative volatility between ethylbenzene and xylene in a distillative fractionation process.

In addition, it is an object of the invention that the process should be simple and cost-efficient to perform and, as far as possible, avoid or at least reduce the use of toxic substances.

The invention is based on the surprising finding that the above objects can be achieved by an extractive distillation process in which an aqueous stream is introduced below a feed stream which comprises a mixture of ethylbenzene and at least one other $C_8$ aromatic compound.

The present invention therefore provides a process for the distillative separation of ethylbenzene from a mixture comprising ethylbenzene and at least one other $C_8$ aromatic compound, comprising:
 a) introducing a feed stream comprising said mixture into a first distillation column,
 b) introducing a first stream comprising a heavy solvent above the feed stream into the first distillation column,
 c) introducing an aqueous stream below the feed stream into the first distillation column.

Of course, during performing the process of the invention, steps a) to c) are, at least for most of the time, carried out simultaneously.

In the process of the present invention, a mixture of ethylbenzene with at least one other $C_8$ aromatic compound is introduced as a feed stream into the first distillation column in step a). The ethylbenzene content of the mixture may vary over a wide range. However, very low ethylbenzene content may cause the process to be less economically attractive.

In one embodiment, the mixture comprises 5 to 99 wt % of ethylbenzene, preferably 10 to 95 wt % of ethylbenzene, more preferably 10 to 85 wt % of ethylbenzene.

The feed stream can, for instance, be introduced into a middle part of the first distillation column.

The feed stream comprises of ethylbenzene and at least one other aromatic compound.

The at least one other $C_8$ aromatic compound is preferably selected from p-xylene, rte-xylene, o-xylene and mixtures thereof.

Preferably, the entire feed to the column is entered as one feed stream into the column, i.e. as the feed stream of step a).

The first stream being introduced into the first distillation column comprises, or preferably consists of, a heavy solvent. The term "heavy solvent" also applies to a mixture of compounds qualifying as heavy solvent(s), and is then denoting the total of such compounds.

The term "heavy solvent" as used herein generally denotes a solvent having a boiling point higher than the boiling point of the at least one other $C_8$ aromatic compound. The heavy solvent has a boiling point preferably above 150° C., more preferably in the range of 151 to 290° C.

The first stream is introduced above the feed stream into the first distillation column in step b).

For example, in case the feed stream is introduced into a middle part of the first distillation column, the first stream is introduced into an upper part of the column.

The heavy solvent preferably comprises, or consists of, at least one Cl, S, N or O-containing compound or a mixture thereof.

The Cl-containing compound is preferably selected from 2,4-dichlorobenzene, 1,2,4-trichlorobenzene, 1,2,4,5-tetrachlorobenzene, polychlorobenzenes, benzene hexachloride, 2,3,4,6-tetrachlorophenol, 1,2,3-trichloropropane and mixtures thereof, and more preferably is selected from 1,2,4-trichlorobenzene and 1,2,3-trichlorobenzene.

The S-containing compound is preferably selected from dimethylsulfoxide, sulfolane, methyl sulfolane and mixtures thereof.

The N-containing compound is preferably selected from N-formylmorpholine, aniline, 2-pyrrolidinone, quinoline, n-methyl-2-pyrrolidone, n-methylaniline, benzonitrile, nitrobenzene and mixtures thereof.

The O-containing compound is preferably selected from methyl salicylate, methylbenzoate, n-methyl-2-pyrrolidone, 1,2-propanediol (propylene glycol), 1,2-butanediol, 1,3-butanediol, benzaldehyde, phenol, tetrahydrofurfuryl alcohol, diethyl maleate, ethyl acetoacetate, 4-methoxy acetophenone, isophorone, 5-methyl-2-hexanone, 2-heptanone, cyclohexanone, 2-octanone, 2-nonanone, 3-heptanone, diisobutyl ketone, 5-nonanone, benzyl alcohol and mixtures thereof.

The aqueous stream is introduced below the feed stream into the first distillation column in step c).

For example, in case the feed stream is introduced into a middle part of the first distillation column, the aqueous stream is introduced into a lower part of the column.

The aqueous stream preferably comprises, or consists of, water and/or steam, and more preferably comprises, or consists of, water.

The amount of the aqueous stream introduced into the distillation column in step c) is preferably so that the mass feed of aqueous stream is from 0.5 to 25 wt %, more preferably from 1 to 20 wt %, still more preferably from 2 to 15 wt %, and most preferably from 4 to 10 wt %, based on the mass feed of the heavy solvent to the distillation column.

In embodiments of the present invention, the aqueous stream comprises, or consists of, water and at least one light solvent selected from Cl, S, N or O-containing compound and mixtures thereof.

The term "light solvent" as used herein generally denotes a solvent having a boiling point lower than the boiling point of the at least one other $C_8$ aromatic compound and lower than the boiling point of ethylbenzene. The term "light solvent" also applies to a mixture of compounds qualifying as light solvent(s), and is then denoting the total of such compounds.

The light solvent has a boiling point preferably lower than 135° C., more preferably lower than 130° C., even more preferably lower than 125° C., still more preferably lower than 120° C., and most preferably lower than 110° C.

The Cl-containing compound is preferably selected from chloroform, carbon tetrachloride and mixtures thereof.

The N-containing compound is preferably selected from dimethylamine, diethylamine, acetonitrile and mixtures thereof.

The O-containing compound is preferably selected from acetaldehyde, 1-propanal, methyl isopropyl ketone, 3-methyl-2-pentanone, 3,3-dimethyl-2-butanone, 2-pentanone, 2-methylpropanal, 1-butanal, cyclopentanone, acetone, ethanol and mixtures thereof.

The process of the present invention is not limited to the separation of ethylbenzene from a mixture comprising ethylbenzene and at least one other $C_8$ aromatic compound, such as o-xylene, p-xylene and m-xylene or mixtures thereof.

In certain embodiments of the process of the present invention, the mixture comprising ethylbenzene and the at least one other $C_8$ aromatic compound further comprises at least one non-aromatic compound and/or at least one further aromatic compound.

The at least one non-aromatic compound can be paraffins, olefins, napthalenes or other aliphatic structure hydrocarbons. Preferably, the at least one non-aromatic compound is selected from C7 to C11 non-aromatic compounds such as isopropylcyclopentane, 2,4,4-trimethylhexane, 2,2-demethylheptane, cis-1,2-dimethylcyclohexane, 1,1,4-trimethylcyclohexane, 2,3,4-trimethylhexane, 1,3,4-trimethylcyclohexane, 2,3-dimethylheptane, 3,5-dimethylheptane, 3,4-dimethylheptane, 2-methyloctane, 3-methyloctane, 1-ethyl-4-methylcyclohexane, ethylcyclohexane, trans-2-nonene, isobutylcyclopentane, 3-ethyl-4-methyl-3-hexene, n-nonane, cis-1-methyl-3-ethylcyclohexane, cyclooctane, isopropylhexane and mixtures thereof.

The at least one further aromatic compound can be benzene, toluene, styrene or mixtures thereof.

Also in certain embodiments, the mixture comprising ethylbenzene and the at least one other C8 aromatic compound may pass through a pretreatment step prior to entering the first distillation column to prepare a feed stream more suitable for the process of the present invention. The pretreatment step may involve, for example, separation of heavy hydrocarbon compounds having 9 Carbon atoms or higher.

The first distillation column is preferably operated at a pressure from 100 mbar to 1100 mbar, more preferably from 140 mbar to 900 mbar. even more preferably from 180 to 700 mbar, and most preferably from 200 to 500 mbar.

The temperature in the first distillation column is preferably from 50 to 250° C., more preferably from 60° C. to 200° C., even more preferably from 70° C. to 180° C.

The amount of heavy solvent introduced into the distillation column in step b) should be high enough to improve the relative volatility of ethylbenzene to the at least one other C8 aromatic compound.

The amount of the heavy solvent stream introduced into the distillation column in step b) is preferably so that a mass feed ratio of heavy solvent to the feed, i.e. the ratio of the total mass of heavy solvent stream to the total mass of the feed stream introduced into the first distillation column, is from 1:1 to 13:1, more preferably from 2:1 to 8:1, still more preferably from 3:1 to 7:1.

In a preferred embodiment, the process according to the invention comprises a step d) in which a second stream enriched in ethylbenzene is withdrawn from the first distillation column, usually from the top or the upper part of the column. The recovery of ethylbenzene, defined as the ratio of ethylbenzene in the second stream to ethylbenzene in the feed stream, is preferably higher than 1, more preferably higher than 1.5, more preferably higher than 2, even more preferably higher than 2.5, still more preferably higher than 3, and most preferably higher than 3.5. Usually, this ratio is not higher than 50.

The second or overhead stream may further comprise water and light solvent. In such a case, the process according to the invention preferably further comprises a step f) of separating the ethylbenzene from the water and light solvent present in the second stream of step d). This can, for example, be done by phase separation in a decanter and/or distillative separation in another distillation column after the overhead stream has been withdrawn.

In a further preferred embodiment, the process according to the invention comprises a step e) in which a third stream enriched in the at least one other C8 aromatic compound and further comprising heavy solvent is withdrawn from the column, usually from the bottom or the lower part of the column.

In an embodiment of the process of the invention, a second distillation column is used. This second column is also referred to as solvent recovery column. In this embodiment, the process preferably further comprises a step g) in which the previously withdrawn third stream of step e) is treated in a second distillation column in order to separate the at least one other C8 aromatic compound from the heavy solvent For reasons of efficiency, streams can be recovered and recycled in the process of the present invention. Streams withdrawn from e.g. the separation unit of step e) and/or the second distillation column of step g) can be recycled into the first distillation column. Preferably, the water and/or the heavy solvent and/or the light solvent is/are recycled to the first distillation column.

The term "reflux ratio" as used herein is defined as the ratio of reflux flow to distillate flow. Preferably, in the first distillation column of the process of the present invention a reflux ratio from 1 to 30, more preferably of 2 to 25, more preferably 4 to 20 and most preferably 5 to 15, is applied.

The present invention also relates to the use of an aqueous stream introduced below a feed stream comprising a mixture of ethylbenzene and at least one other $C_8$ aromatic compound in a distillative separation of ethylbenzene from said mixture for increasing the efficiency of the separation.

The present invention will be further illustrated by an example described below, and by reference to the following FIGURE:

FIG. 1 shows a typical process flow scheme in accordance with one embodiment of the present invention.

EXTRACTIVE DISTILLATION PROCESS SCHEME

An exemplary process flow scheme for simulating the process according to one embodiment of this invention will be explained hereinunder by reference to FIG. 1.

Three streams are introduced into an extractive distillation column 10, which is also referred to as first distillation column. The internal of the first distillation column can be variously chosen to get a desired efficiency, for example the distillation column may be filled with a number of packed beds or trays.

A feed stream 11 comprising a mixture comprising ethylbenzene and at least one other C8 aromatic compound is introduced into the column 10 via a conduit, for instance in a middle portion of the column. The temperature of the mixture may be adjusted as needed, for instance using a heat exchanger. Simultaneously, a first stream 12 comprising a heavy solvent and an aqueous stream 13 comprising water are introduced into the first distillation column 10 via two respective conduits. The first stream 12 is introduced above the feed stream 11, for instance in an upper portion of the column 10, whereas the aqueous stream 13 is simultaneously introduced below the feed stream 11, for instance in a lower portion of the column 10.

The heavy solvent will preferentially form a higher boiling point mixture with the at least one other C8 aromatic compound and be distilled down the first distillation column 10, whereas the lighter boiling ethylbenzene which has less affinity with the heavy solvent will be distilled up the column.

From the top or upper part of the first column a second stream 14 comprising ethylbenzene, water and optionally light solvent, is withdrawn. This second stream can be introduced into a phase separator 20, wherein the ethylbenzene is separated from water. A stream comprising the separated ethylbenzene, which is also referred to as ethylbenzene rich stream, part of which may then be recycled into the first distillation column as reflux 21 or simply passed to storage 22. The separated water can also be further used, or recycled into the first distillation column 10 as aqueous stream 23 as shown in FIG. 1.

From the bottom of the first column 10 a third stream 15 comprising heavy solvent and the at least one other C8 aromatic compound is withdrawn. This third stream 15 may also comprise small and less amounts of ethylbenzene. The third stream can be introduced into a solvent recovery column 30, which is also referred to as second distillation column. Therein, the at least one other C8 aromatic compound is separated from the heavy solvent. From the bottom of the solvent recovery column 30, heavy solvent is withdrawn which can be recycled into the first distillation column 10 as first stream 32.

From the top of the solvent recovery column 30, a stream 31 comprising the at least one other C8 aromatic compound and probably minor amounts of ethylbenzene is withdrawn. This stream is also referred to as ethylbenzene lean stream.

Additional equipment such as heat exchanger, pump or compressor may be added to any appropriate location of the process system in order to properly adjust condition of the process. Suitable dimension and configuration of all equipment in the process can be modified by those having ordinary skills in the art to match with the exact composition of the feed stream, the extractive agent and specific operating conditions employed.

Embodiments of the present invention are further described in the following example.

EXAMPLE 1

A computer simulation has been performed using the simulation software "Aspen HYSYS®", simulating that a feed stream containing 14.66 wt % ethylbenzene, 20.21 wt % p-xylene, 43.35 wt % m-xylene and 21.78 wt % o-xylene was fed at a feed rate of 133 g/min to an extractive distillation column having 18 stages. Various solvents as shown in Table 1 were introduced to the extractive distillation column at stage 2, i.e. a location above the point of introduction of the feed stream at stage 10. As a comparative example, a simulation has been run where no solvent is introduced. The operating temperatures were simulated along the column within the range of 75° C. to 175° C. The pressure in the column was simulated to be 200 mbar and 1000 mbar, respectively (see Table 1 below). The weight ratio of the solvent to the feed stream was fixed at 5:1. The simulation model further included the features that an ethylbenzene-rich stream was withdrawn at the top of the column and an ethylbenzene-lean stream was withdrawn at the bottom of the column. A portion of the ethylbenzene-rich stream from the top of the column was simulated to be returned to the column as reflux at a reflux ratio of 10.

To demonstrate the effect of addition of water to the column, it has been simulated that water is introduced above ("water above") and below ("water below") the feed stream, respectively, at a rate of 36 g/min. For comparison, it has also been simulated that no water is introduced into the column. The results are shown in the following Table 1 below.

It can be seen in Table 1 that the introduction of water into the system improves the separation efficiency of the process at an operating pressure of 200 mbar and 1000 mbar, respectively, and for all solvents employed. It has been found that a higher ethylbenzene content was obtained in the overhead stream withdrawn from the top of the column ("EB concentration in overhead"). In particular, a higher efficiency was found when the water was introduced at a location below the introduction point of the feed stream according to the present invention ("water below").

In table 1 below, TCB is 1,2,4-trichlorobenzene, and NMP is n-methyl-2-pyrrolidone.

TABLE 1

| Solvent with 5 wt % water | EB conc. in overhead wt % | EB conc. in overhead wt % | EB conc. in overhead wt % | EB conc. in overhead wt % | EB conc. in overhead wt % | EB conc. in overhead wt % |
|---|---|---|---|---|---|---|
| WATER OPTIONS | NO WATER | WATER ABOVE | WATER BELOW | NO WATER | WATER ABOVE | WATER BELOW |
| TOP PRESSURE [mbar] | 200 | 200 | 200 | 1000 | 1000 | 1000 |
| NO SOLVENT | 24.80 | 25.35 | 25.86 | 22.78 | 23.53 | 24.04 |
| TCB | 30.50 | 31.82 | 37.83 | 27.40 | 28.49 | 32.35 |
| NITROBENZENE | 56.01 | 56.26 | 56.53 | 54.25 | 54.51 | 54.96 |
| ISOPHORONE | 38.32 | 38.86 | 39.82 | 34.90 | 35.30 | 36.35 |
| METHYL-SALICYLATE | 44.85 | 46.28 | 50.00 | 27.39 | 28.49 | 32.34 |
| BENZALDEHYDE | 30.60 | 31.93 | 32.46 | 27.78 | 28.49 | 29.92 |
| SULFOLANE | 26.99 | 27.49 | 28.94 | 25.35 | 25.79 | 26.94 |
| NMP | 37.47 | 38.58 | 41.04 | 33.12 | 34.62 | 36.85 |

The invention claimed is:

1. A process for the distillative separation of ethylbenzene from a mixture comprising ethylbenzene and at least one other C8 aromatic compound selected from the group consisting of p-xylene, m-xylene, o-xylene, and mixtures thereof, the process comprising:
    a) introducing a feed stream comprising said mixture into a first distillation column;
    b) introducing a first stream comprising a heavy solvent above the feed stream into the first distillation column; and
    c) introducing an aqueous stream below the feed stream into the first distillation column, wherein the aqueous stream comprises water and at least one light solvent includes one or more Cl, S, N or O-containing compounds.

2. The process according to claim 1, wherein the heavy solvent comprises at least one Cl, S, N or O-containing compound, or mixtures thereof.

3. The process according to claim 2, wherein the Cl-containing heavy solvent compound is selected from the group consisting of 2,4-dichlorobenzene, 1,2,3-trichlorobenzene, 1,2,4-trichlorobenzene, 1,2,4,5-tetrachlorobenzene, polychlorobenzenes, benzene hexachloride, 2,3,4,6-tetrachlorophenol, 1,2,3-trichloropropane, and mixtures thereof.

4. The process according to claim 2, wherein the S-containing heavy solvent compound is selected from the group consisting of dimethylsulfoxide, sulfolane, methyl sulfolane, and mixtures thereof.

5. The process according to claim 2, wherein the N-containing heavy solvent compound is selected from the group consisting of N-formylmorpholine, aniline, 2-pyrolidinone, quinoline, n-methyl-2-pyrrolidone, n-methylaniline, benzonitrile, nitrobenzene, and mixtures thereof.

6. The process according to claim 2, wherein the O-containing heavy solvent compound is selected from the group consisting of methyl salicylate, metylbenzoate, n-methyl-2-pyrrolidone, 1,2-propanediol (propylene glycol), 1,2-butanediol, 1,3-butanedlol, benzaldehyde, phenol, tetrahydrofurforyl alcohol, diethyl maleate, ethyl acetoacetate, 4-methoxy acetophenone, isophorone, 5-methyl-2-hexanone, 2-heptanone, cyclohexanone, 2-octanone, 2-nonanone, 3-heptanone, diisobutyl ketone, 5-nonanone, benzyl alcohol, and mixtures thereof.

7. The process according to claim 1, wherein the aqueous stream includes steam.

8. The process according to claim 1, wherein the Cl-containing light solvent compound is selected from the group consisting of chloroform, carbon tetrachloride, and mixtures thereof.

9. The process according to claim 1, wherein the N-containing light solvent compound includes one or more of dimethylamine, diethylamine, or acetonitrile.

10. The process according to claim 1, wherein the O-containing light solvent compound is selected from the group consisting of acetaldehyde, 1-propanal, methyl isopropyl ketone, 3-methyl-2-pentanone, 3,3-dimethyl-2-butanone, 2-pentanone, 2- methylpropanal, 1-butanal, cyclopentanone, acetone, ethanol, and mixtures thereof.

11. The process according to claim 1, wherein the mass feed of the aqueous stream is from 0.5 to 25 wt % based on a mass feed of the heavy solvent.

12. The process according to claim 1, wherein the mass feed ratio of heavy solvent to the feed is from 1:1 to 10:1.

13. The process according to claim 1, further comprising:
    d) withdrawing a second stream enriched in ethylbenzene from the first distillation column.

14. The process according to claim 1 wherein the heavy solvent is selected from one or more aromatic solvents.

15. The process according to claim 3, wherein the Cl-containing heavy solvent compound is selected from the group consisting of 1,2,4- trichlorobenzene, 1,2,3-trichlorobenzene, and mixtures thereof.

16. A process for the distillative separation of ethylbenzene from a mixture comprising ethylbenzene and at least one other $C_8$ aromatic compound, the process comprising:

a) introducing a feed stream comprising said mixture into a first distillation column;
b) introducing a first stream comprising a heavy solvent above the feed stream into the first distillation column; and
c) introducing an aqueous stream below the feed stream into the first distillation column, the aqueous stream having a mass feed from 5 wt % to 25 wt % based on a mass feed of the heavy solvent, and wherein the aqueous stream comprises water and at least one light solvent including one or more Cl, S, N or O-containing compounds.

17. The method of claim 16 wherein the mass feed of the aqueous stream is from 5 wt % to 10 wt % based on the mass feed of the heavy solvent.

18. A process for the distillative separation of ethylbenzene from a mixture comprising ethylbenzene and at least one other C8 aromatic compound selected from the group consisting of p-xylene, m-xylene, o-xylene, and mixtures thereof, the process comprising:
a) introducing a feed stream comprising said mixture into a first distillation column;
b) introducing a first stream comprising a heavy solvent above the feed stream into the first distillation column, wherein the heavy solvent is selected from the group consisting of 2,4-dichlorobenzene, 1,2,3-trichlorobenzene, 1,2,4-trichlorobenzene, 1,2,4,5-tetrachlorobenzene, polychlorobenzenes, benzene hexachloride, 2,3,4,6-tetrachlorophenol, 1,2,3-trichloropropane, and mixtures thereof; and
c) introducing an aqueous stream below the feed stream into the first distillation column.

19. The method of claim 1, further comprising heating the distillation column to a temperature in a range of 50° C. to 250° C.

* * * * *